US00PP28457P2

(12) United States Plant Patent
Heiser

(10) Patent No.: US PP28,457 P2
(45) Date of Patent: Sep. 26, 2017

(54) ***PETUNIA* PLANT NAMED 'BHTUN65301'**

(50) Latin Name: *Petunia×hybrida*
Varietal Denomination: BHTUN65301

(71) Applicant: Brian Heiser, Escondido, CA (US)

(72) Inventor: Brian Heiser, Escondido, CA (US)

(73) Assignee: Plant 21 LLC, Bonsall, CA (US)

( * ) Notice: Subject to any disclaimer, the term of this patent is extended or adjusted under 35 U.S.C. 154(b) by 0 days.

(21) Appl. No.: 14/999,655

(22) Filed: Jun. 9, 2016

(51) Int. Cl.
*A01H 5/02* (2006.01)

(52) U.S. Cl.
USPC ..... Plt./356.21

(58) Field of Classification Search
USPC ..... Plt./356.21, 356.22
CPC ..... A01H 5/02
See application file for complete search history.

*Primary Examiner* — Kent L Bell
(74) *Attorney, Agent, or Firm* — C. A. Whealy

(57) ABSTRACT

A new and distinct *Petunia* plant named 'BHTUN65301', characterized by its relatively tall, upright to outwardly spreading and mounding plant habit; vigorous growth habit; freely branching habit; early and freely flowering habit; long flowering period; fuchsia purple-colored flowers; and good garden performance.

1 Drawing Sheet

Botanical designation: *Petunia×hybrida.*
Cultivar denomination: 'BHTUN65301'.

BACKGROUND OF THE INVENTION

The present invention relates to a new and distinct cultivar of *Petunia* plant, botanically known as *Petunia×hybrida* and hereinafter referred to by the name 'BHTUN65301'.

The new *Petunia* plant is a product of a planned breeding program conducted by the Inventor in Bonsall, Calif. The objective of the breeding program is to create new freely-branching, vigorous and uniformly mounding *Petunia* plants with early and freely flowering habit, unique attractive flowers and good garden performance.

The new *Petunia* plant originated from a cross-pollination made by the Inventor on Nov. 30, 2013 in Bonsall, Calif. of a proprietary seedling selection of *Petunia×hybrida* identified as code number 13PC477-02, not patented, as the female, or seed, parent with *Petunia×hybrida* 'USTUNI8902', disclosed in U.S. Plant Pat. No. 17,895, as the male, or pollen, parent. The new *Petunia* plant was discovered and selected by the Inventor as a single flowering plant within the progeny of the stated cross-pollination in a controlled greenhouse environment in Bonsall, Calif. on Jul. 3, 2014.

Asexual reproduction of the new *Petunia* plant by vegetative terminal cuttings in a controlled greenhouse environment in Bonsall, Calif. since Jul. 3, 2014 has shown that the unique features of this new *Petunia* plant are stable and reproduced true to type in successive generations.

SUMMARY OF THE INVENTION

Plants of the new *Petunia* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'BHTUN65301'. These characteristics in combination distinguish 'BHTUN65301' as a new and distinct *Petunia* plant:

1. Relatively tall, upright to outwardly spreading and mounding plant habit.
2. Vigorous growth habit.
3. Freely branching habit.
4. Early and freely flowering habit; long flowering period.
5. Fuchsia purple-colored flowers
6. Good garden performance.

Plants of the new *Petunia* can be compared to plants of the female parent selection. In side-by-side comparisons, plants of the new *Petunia* differ primarily from plants of the female parent selection in the following characteristics:

1. Plants of the new *Petunia* are more freely branching than plants of the female parent selection.
2. Plants of the new *Petunia* are more freely flowering than plants of the female parent selection.
3. Flowers of plants of the new *Petunia* are darker fuchsia purple in color than flowers of plants of the female parent selection.

Plants of the new *Petunia* can be compared to plants of the male parent, 'USTUNI8902'. In side-by-side comparisons, plants of the new *Petunia* differ primarily from plants of 'USTUNI8902' in the following characteristics:

1. Plants of the new *Petunia* have narrower leaves than plants of 'USTUNI8902'.
2. Flowers of plants of the new *Petunia* are deeper fuchsia purple in color than flowers of plants of 'USTUNI8902'.

Plants of the new *Petunia* can be compared to plants of 'USTUNI6001', disclosed in U.S. Plant Pat. No. 17,730. In side-by-side comparisons, plants of the new *Petunia* differ primarily from plants of 'USTUNI6001' in the following characteristics:

1. Plants of the new *Petunia* are taller than plants of 'USTUNI6001'.

2. Plants of the new *Petunia* and 'USTUNI6001' differ in flower color as plants of 'USTUNI6001' have bright pink-colored flowers with red purple-colored venation.

Plants of the new *Petunia* can be compared to plants of 'USTUN34803', disclosed in U.S. Plant Pat. No. 22,884. In side-by-side comparisons, plants of the new *Petunia* differ primarily from plants of 'USTUN34803' in the following characteristics:

1. Plants of the new *Petunia* are taller than plants of 'USTUN34803'.
2. Plants of the new *Petunia* have larger flowers than plants of 'USTUN34803'.

BRIEF DESCRIPTION OF THE PHOTOGRAPHS

The accompanying colored photographs illustrate the overall appearance of the new *Petunia* plant showing the colors as true as it is reasonably possible to obtain in colored reproductions of this type. Colors in the photographs may differ slightly from the color values cited in the detailed botanical description which accurately describe the colors of the new *Petunia* plant.

The photograph at the bottom of the sheet is a side perspective view of a typical flowering plant of 'BHTUN65301' grown in a container.

The photograph at the top of the sheet is a close-up view of a typical flowering plant of 'BHTUN65301'.

DETAILED BOTANICAL DESCRIPTION

The aforementioned photographs and following observations, measurements and values describe plants grown during the spring in 10-cm containers in an acrylic-covered greenhouse in Carleton, Mich. During the production of the plants, day and night temperatures ranged from 18° C. to 30° C. and light levels averaged 1,500 foot candles. Plants were seven weeks old when the photographs and description were taken. In the following description, color references are made to The Royal Horticultural Society Colour Chart, 2007 Edition, except where general terms of ordinary dictionary significance are used.

Botanical classification: *Petunia×hybrida* 'BHTUN65301'.

Parentage:

*Female, or seed, parent*.—Proprietary seedling selection of *Petunia×hybrida* identified as code number 13PC477-02, not patented.

*Male, or pollen, parent*.—*Petunia×hybrida* 'USTUNI8902', disclosed in U.S. Plant Pat. No. 17,895.

Propagation:

*Type*.—Terminal vegetative cuttings.

*Time to produce a rooted young plant, summer*.—About 15 days at ambient temperatures ranging from 16° C. to 29° C.

*Time to produce a rooted young plant, winter*.—About 20 days at ambient temperatures ranging from 16° C. to 21° C.

*Root description*.—Medium in thickness, fibrous; white in color, actual color of the roots is dependent on substrate composition, water quality, fertilizer type and formulation, substrate temperature and physiological age of roots.

*Rooting habit*.—Freely branching; medium density.

Plant description:

*Plant and growth habit*.—Relatively tall, upright to outwardly spreading and mounding plant habit; freely branching habit with about eight primary lateral branches each with about three secondary lateral branches developing per plant; dense and bushy appearance; vigorous growth habit.

*Plant height, soil level to top of foliar plane*.—About 15 cm.

*Plant height, soil level to top of floral plane*.—About 18 cm.

*Plant diameter* (*area of spread*).—About 29 cm.

*Lateral branches*.—Length: About 18 cm. Diameter: About 3 mm. Internode length: About 7 mm to 18 mm. Strength: Strong. Aspect: Initially upright then about 55 to 60° from vertical. Texture and luster: Pubescent; matte. Color, developing: Close to 144A. Color, developed: Close to 146B.

Leaf description:

*Arrangement*.—Alternate before flowering; opposite after flowers develop; leaves simple.

*Length*.—About 5.8 cm.

*Width*.—About 2.6 cm.

*Shape*.—Elliptical.

*Apex*.—Acute.

*Base*.—Attenuate.

*Margin*.—Entire.

*Texture and luster, upper and lower surfaces*.—Pubescent; matte.

*Venation pattern*.—Pinnate, arcuate.

*Color*.—Developing leaves, upper surface: Close to 137A. Developing leaves, lower surface: Close to 146B. Fully expanded leaves, upper surface: Close to 137A; venation, close to 146C. Fully expanded leaves, lower surface: Close to 146B; venation, close to 146C.

*Petioles*.—Length: About 1.3 cm. Diameter: About 3 mm. Strength: Moderately strong. Texture and luster, upper and lower surfaces: Pubescent, minute; slightly glossy. Color, upper and lower surfaces: Close to 146B.

Flower description:

*Flower type and flowering habit*.—Single axillary salverform flowers; flowers face mostly upward to outwardly; freely flowering habit with about 120 flower buds and open flowers per plant at one time.

*Natural flowering season*.—Long day responsive; early flowering habit and long flowering period, plants flower from early spring until frost in the autumn, flowering continuous during this period.

*Flower longevity on the plant*.—About four to five days; flowers persistent.

*Fragrance*.—Faintly fragrant; spicy and sweet.

*Flower buds*.—Length: About 3 cm. Diameter: About 8 mm. Shape: Oblong, elongate Texture and luster: Smooth, glabrous; slightly glossy. Color: Close to N77D.

*Flower diameter*.—About 4.3 cm.

*Flower depth* (*height*).—About 3.8 cm.

*Throat diameter, distal*.—About 8 mm.

*Tube length*.—About 2.6 cm.

*Tube diameter*.—Proximal, about 3 mm; distally, about 8 mm.

*Petals*.—Quantity and arrangement: Five petals fused in a single salverform whorl. Petal lobe length (from throat): About 2 cm. Petal lobe width: About 2 cm. Petal lobe shape: Fan-shaped. Petal lobe apex: Acute. Petal lobe margin: Entire; initially undulate and flattening with development. Petal lobe texture and luster, upper surface: Smooth, glabrous; matte. Petal lobe texture and luster, lower surface: Scattered pubescence along the venation; matte. Throat texture and luster: Smooth, glabrous; glossy. Tube texture and luster: Pubescent; prominent venation; matte. Color: When opening, upper surface: Close to 72A. When opening, lower surface: More grey than 76A. Fully opened, upper surface: Close to 64A; venation, close to 71A; with development, a star-shape pattern develops with close to N78A to N78B where the petal lobes meet. Fully opened, lower surface: Close to 70B; venation, close to 194A; color becoming more grey than N81C with development. Flower throat (inside): Close to 64A; venation, close to 71A. Flower tube (outside): Close to 70B; venation, close to 195A.

*Sepals*.—Quantity and arrangement: Five sepals fused in a single star-shaped whorl. Length: About 2 cm. Width: About 3 mm. Shape: Lanceolate. Apex: Acute; reflexed. Margin: Entire. Texture and luster, upper and lower surfaces: Pubescent; matte. Color: When opening, upper and lower surfaces: Close to 144A. Fully opened, upper surface: Close to 137A. Fully opened, lower surface: Close to 137B.

*Peduncles*.—Length: About 2.6 cm. Width: About 2 mm. Strength: Strong. Angle: About 35° to 45° from the stem axis. Texture and matte: Pubescent; minute; matte. Color: Close to 146C.

*Reproductive organs*.—Stamens: Quantity per flower: Five. Filament length: About 1.5 cm. Filament color: Close to 145D. Anther length: About 1.5 mm. Anther shape: Oval. Anther color: Close to 201C. Pollen amount: Moderate. Pollen color: Close to 202B. Pistils: Quantity per flower: One. Pistil length: About 2.2 cm. Style length: About 2 cm. Style color: Close to 145D. Stigma diameter: About 2 mm. Stigma shape: Round to oval. Stigma color: Close to 201A. Ovary color: Close to 144A.

*Seeds and fruits*.—Seed and fruit development has not been observed on plants of the new *Petunia*.

Pathogen & pest resistance: Plants of the new *Petunia* have not been noted to be resistant to pathogens or pests common to *Petunia* plants.

Garden performance: Plants of the new *Petunia* have been observed to have good garden performance and have been observed to tolerate rain, wind and low temperatures about 2° C. and to be suitable for USDA Hardiness Zone 10.

It is claimed:

1. A new and distinct *Petunia* plant named 'BHTUN65301' as illustrated and described.

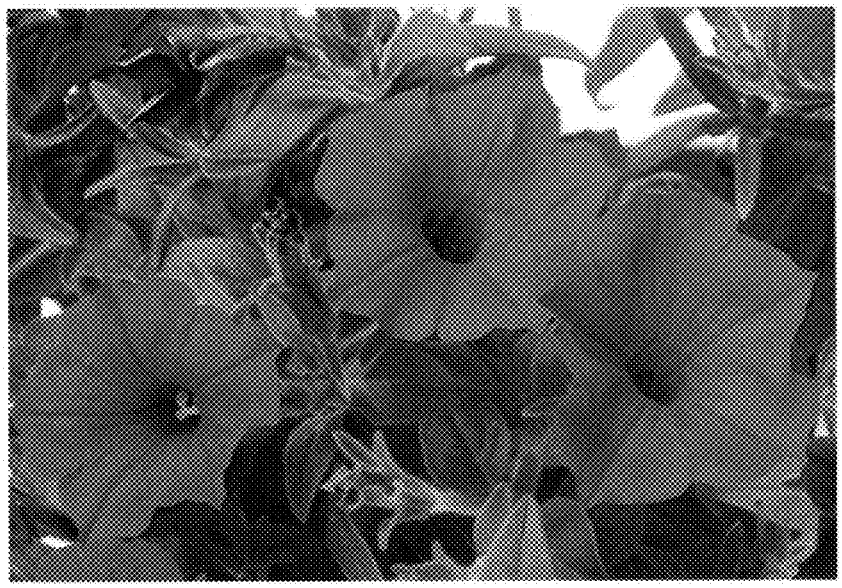
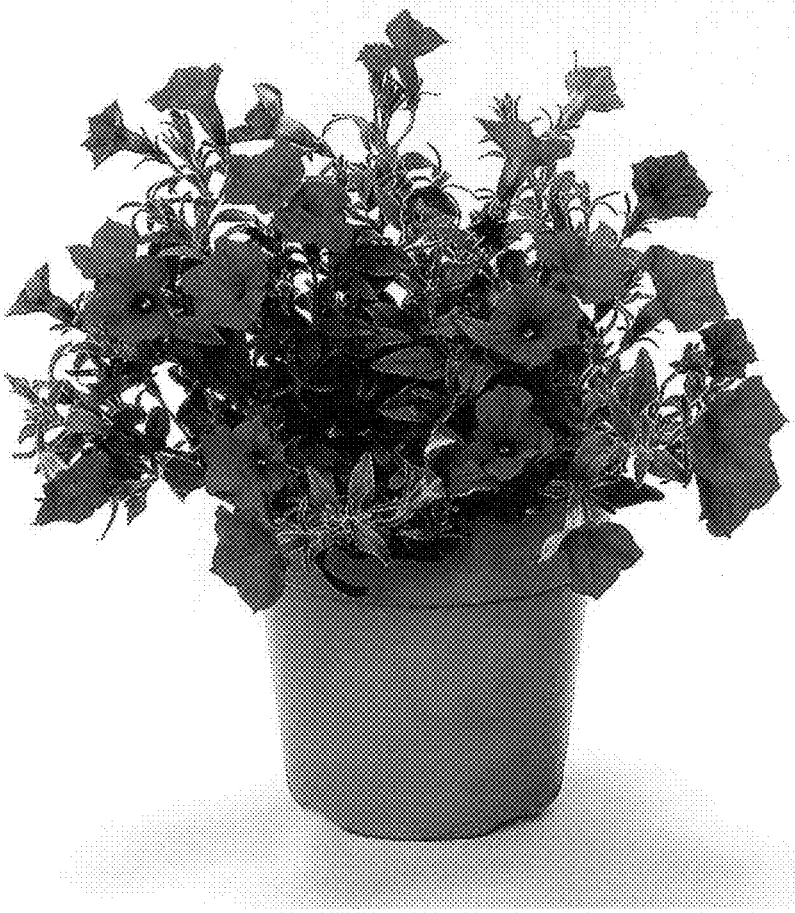

* * * * *